(12) United States Patent
Hacker et al.

(10) Patent No.: US 8,158,559 B2
(45) Date of Patent: *Apr. 17, 2012

(54) HERBICIDAL COMBINATION COMPRISING DIMETHOXYTRIAZINYL-SUBSTITUTED DIFLUOROMETHANESULFONYLANILIDES

(75) Inventors: Erwin Hacker, Hochheim (DE); Christian Waldraff, Bad Vilbel (DE); Christopher Hugh Rosinger, Hofheim (DE); Chieko Ueno, Frankfurt (DE); Georg Bonfig-Picard, Rodenbach (DE); Stefan Schnatterer, Hattersheim (DE); Shinichi Shirakura, Oyama (JP)

(73) Assignee: Bayer Cropscience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,499

(22) Filed: Mar. 22, 2011

(65) Prior Publication Data

US 2011/0172100 A1 Jul. 14, 2011

Related U.S. Application Data

(63) Continuation of application No. 12/540,244, filed on Aug. 12, 2009.

(30) Foreign Application Priority Data

Aug. 14, 2008 (DE) .......................... 10 2008 037 631

(51) Int. Cl.
*A01N 43/64* (2006.01)
*A01N 43/60* (2006.01)

(52) U.S. Cl. ........................................ 504/134; 504/136

(58) Field of Classification Search .................. 504/134, 504/136

See application file for complete search history.

(56) References Cited

U.S. PATENT DOCUMENTS

| | | | |
|---|---|---|---|
| 6,054,410 A | 4/2000 | Landes et al. | |
| 2003/0060367 A1 | 3/2003 | Bieringer et al. | |
| 2007/0167328 A1* | 7/2007 | Endo et al. .................... | 504/104 |
| 2010/0062939 A1 | 3/2010 | Hacker et al. | |
| 2010/0062941 A1 | 3/2010 | Hacker et al. | |
| 2010/0069246 A1 | 3/2010 | Hacker et al. | |
| 2010/0069248 A1 | 3/2010 | Hacker et al. | |
| 2010/0069249 A1 | 3/2010 | Hacker et al. | |
| 2010/0075852 A1 | 3/2010 | Hacker et al. | |
| 2010/0075854 A1 | 3/2010 | Hacker et al. | |
| 2010/0093541 A1 | 4/2010 | Hacker et al. | |
| 2010/0093542 A1 | 4/2010 | Hacker et al. | |
| 2010/0234226 A1 | 9/2010 | Hacker et al. | |

FOREIGN PATENT DOCUMENTS

| | | |
|---|---|---|
| CA | 2 670 240 | 5/2008 |
| DE | 195 21 355 A1 | 12/1996 |
| DE | 195 34 910 A1 | 3/1997 |
| DE | 10 2008 037 630 A1 | 2/2010 |
| JP | 11-60562 A1 | 3/1999 |
| JP | 2001-245688 A | 9/2001 |
| WO | 93/09099 A2 | 5/1993 |
| WO | 96/41799 A1 | 12/1996 |
| WO | 00/06553 A1 | 10/2000 |
| WO | 03/015520 A1 | 2/2003 |
| WO | 2005/096818 A1 | 10/2005 |
| WO | 2007/031208 A2 | 3/2007 |
| WO | 2008/101595 A2 | 8/2008 |
| WO | 2009/024251 A2 | 2/2009 |
| WO | 2010/017921 A2 | 2/2010 |
| WO | 2010/017922 A2 | 2/2010 |
| WO | 2010/017923 A2 | 2/2010 |
| WO | 2010/017924 A2 | 2/2010 |

(Continued)

OTHER PUBLICATIONS

Saflufenacil, Copyright © 1995-2011 Alan WoodDatabase right Alan Wood (maker)—first published 1995, [online], [retrieved on Apr. 7, 2011]. Retrieved from the Internet:<URL: http://www.alanwood.net/pesticides/saflufenacil.html>.*

Amide Herbicides, Copyright © 1995-2011 Alan WoodDatabase right Alan Wood (maker)—first published 1995, [online], [retrieved on Apr. 7, 2011]. Retrieved from the Internet:<URL: http://www.alanwood.net/pesticides/class_herbicides.html#amide_herbicides>.*

(Continued)

*Primary Examiner* — Janet Epps-Smith
*Assistant Examiner* — Courtney Brown
(74) *Attorney, Agent, or Firm* — Baker Donelson Bearman Caldwell & Berkowitz PC

(57) ABSTRACT

The present invention relates to a herbicide combination comprising components (A) and (B) where
(A) denotes one or more compounds or salts thereof from the group described by the general formula (I):

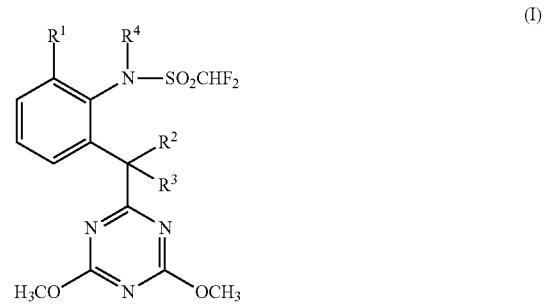

in which
$R^1$ is halogen, preferably fluorine or chlorine,
$R^2$ is hydrogen and $R^3$ is hydroxyl or
$R^2$ and $R^3$ together with the carbon atom to which they are attached are a carbonyl group C=O and
$R^4$ is hydrogen or methyl;
and
(B) denotes one or more herbicides from the group of the pyrimidines consisting of: (B1-1) ancymidol, (B1-2) flurprimidol, (B1-3) pyrimisulfan, (B2-1) bispyribac-sodium, (B2-2) pyribenzoxim, (B2-3) pyriminobac-methyl, (B2-4) pyribambenz-isopropyl, (B2-5) pyribambenz-propyl, (B3-1) pyriftalid, (B3-2) pyrithiobac-sodium, (B4-1) benzfendizone, (B4-2) bromacil, (B4-3) butafenacil, (B4-4) lenacil, (B4-5) terbacil, (B4-6) SYN-523, (B4-7) saflufenacil.

19 Claims, No Drawings

| | FOREIGN PATENT DOCUMENTS | | |
|---|---|---|---|
| WO | 2010/017925 | A2 | 2/2010 |
| WO | 2010/017926 | A2 | 2/2010 |
| WO | 2010/017927 | A2 | 2/2010 |
| WO | 2010/017928 | A1 | 2/2010 |
| WO | 2010/017929 | A1 | 2/2010 |
| WO | 2010/017930 | A2 | 2/2010 |
| WO | 2010/017931 | A2 | 2/2010 |
| WO | 2010/127786 | A1 | 11/2010 |
| ZA | 96/4943 | | 12/1996 |

OTHER PUBLICATIONS

International Search Report of PCT/EP2009/005764 mailed Feb. 3, 2011.

C D S Tomlin "The Pesticide Manual", A World Compendium, vol. 15 (2009), 7 pages.

* cited by examiner

HERBICIDAL COMBINATION COMPRISING DIMETHOXYTRIAZINYL-SUBSTITUTED DIFLUOROMETHANESULFONYLANILIDES

CROSS REFERENCE TO RELATED APPLICATIONS

This application is a continuation application of U.S. patent application Ser. No. 12/540,244 (the entire disclosure of which is incorporated herein by reference), filed on Aug. 12, 2009, which claim priority to German Application No. 10 2008 037 631.0 filed Aug. 14, 2008.

BACKGROUND OF THE INVENTION

1. Field of the Invention

The present invention is in the technical field of crop protection compositions which can be used against unwanted vegetation, for example by the pre-sowing method (with or without incorporation), by the pre-emergence method or by the post-emergence method in sown or planted crop plants such as, for example, in wheat (durum wheat and common wheat), corn, soybeans, sugar beet, sugar cane, cotton, rice (planted or sown under upland or paddy conditions using indica or japonica varieties and also hybrids/mutants/GMOs), beans (such as, for example, bush beans and broad beans), flax, barley, oats, rye, triticale, oilseed rape, potatoes, millet (sorghum), pasture grass, greens/lawns, in fruit plantations (plantation crops) or on non-crop areas (for example squares of residential areas or industrial sites, rail tracks). In addition to the single application, sequential applications are also possible.

It relates to a herbicide combination comprising at least two herbicides and to their use for controlling unwanted vegetation, in particular a herbicide combination comprising N-{2-[4,6-dimethoxy-(1,3,5)triazine-2-(carbonyl- or -hydroxymethyl)]-6-halophenyl}difluoromethanesulfonamides or their N-methyl derivatives and/or their salts, hereinbelow also referred to as "dimethoxytriazinyl-substituted difluoromethanesulfonylanilides", and to herbicidally active compounds from the group of the pyrimidines.

2. Description of Related Art

It is known that cyclicly substituted sulfonamides have herbicidal properties (for example WO 93/09099 A2, WO 96/41799 A1). These also include the phenyldifluoromethanesulfonamides, which are also referred to as difluoromethanesulfonylanilides. The last mentioned compounds are, for example, phenyl derivatives which are mono- or polysubstituted, inter alia by dimethoxypyrimidinyl (for example WO 00/006553 A1) or dimethoxytriazinyl and also a further halogen substitution (for example WO 2005/096818 A1, WO 2007/031208 A2).

However, specific compounds from the group of the N-{2-[4,6-dimethoxy-(1,3,5)triazine-2(-carbonyl- or -hydroxymethyl)]-6-halophenyl}difluoromethanesulfonamides, as described in WO 2005/096818 A1, and their N-methyl derivatives, as described for the first time in WO 2006/008159 A1 in connection with fungicides and in WO 2007/031208 A2 and JP 2007-213330 (unpublished) as herbicides, are not entirely satisfactory in all respects with regard to their herbicidal properties.

The herbicidal activity of the dimethoxytriazinyl-substituted difluoromethanesulfonylanilides against harmful plants (broad-leaved weeds, weed grasses, Cyperaceae; hereinbelow collectively also referred to as "weed") is already at a high level, but depends in general on the application rate, the formulation in question, the harmful plants to be controlled in each case or the spectrum of harmful plants, the climatic and soil conditions and the like. Further criteria in this context are duration of action, or the breakdown rate, of the herbicide, the general crop plant compatibility and the speed of action (more rapid onset of action), the activity spectrum and behaviour toward follower crops (replanting problems) or the general flexibility of application (control of weeds in their various growth stages). If appropriate, changes in the susceptibility of harmful plants, which may occur on prolonged use of the herbicides or in limited geographical regions (control of tolerant or resistant weed species) may also have to be taken into account. The compensation of losses in action in the case of individual plants by increasing the application rates of the herbicides is only possible to a certain degree, for example because such a procedure reduces the selectivity of the herbicides or because the action is not improved, even when applying higher rates.

Thus, there is frequently a need for targeted synergistic activity against specific weed species, weed control with better overall selectivity, generally lower amounts of active compounds used for equally good control results and for a reduced active compound input into the environment to avoid, for example, leaching and carry-over effects. There is also a need for developing one-shot applications to avoid labor-intensive multiple applications, and also to develop systems for controlling the rate of action, where, in addition to an initial rapid control of weeds there is also a slower, residual control.

A possible solution to the problems mentioned above may be to provide herbicide combinations, that is mixtures of a plurality of herbicides and/or other components from the group of the agrochemically active compounds of a different type and of formulation auxiliaries and additives customary in crop protection which contribute the desired additional properties. However, in the combined use of a plurality of active compounds, there are frequently phenomena of chemical, physical or biological incompatibility, for example lack of stability of a joint formulation, decomposition of an active compound or antagonism in the biological activity of the active compounds. For these reasons, potentially suitable combinations have to be selected in a targeted manner and tested experimentally for their suitability, it not being possible to safely discount a priori negative or positive results.

Mixtures of non-N-methyl derivatives of the compounds mentioned above are known in principle (for example WO 2007/079965 A2); however, their effectiveness in mixtures with other herbicides has only been confirmed in individual cases for dimethoxypyimidinyl-substituted phenyl derivatives. In addition, there are also mixtures of selected N-methyl derivatives of the compounds mentioned above with some combination partners (PCT/EP2008/000870, unpublished).

BRIEF SUMMARY OF THE INVENTION

It was the object of the present invention to provide crop protection compositions as alternatives to the prior art, or as an improvement thereof.

Surprisingly, it has now been found that this object can be achieved by herbicide combinations of dimethoxytriazinyl-substituted difluoromethanesulfonylanilides in combination with structurally different herbicides from the group of the pyrimidines which act together in a particularly □avourable manner, for example when they are used for controlling unwanted vegetation in sown and/or planted crop plants such as wheat (durum wheat and common wheat), corn, soybeans, sugar beet, sugar cane, cotton, rice (planted or sown under upland or paddy conditions using indica and/or japonica varieties and also hybrids/mutants/GMOs), beans (such as, for example, bush beans and broad beans), flax, barley, oats, rye, triticale, oilseed rape, potatoes, millet (sorghum), pasture grass, greens/lawns, in fruit plantations (plantation crops) or on non-crop areas (for example squares of residential areas or industrial sites, rail tracks), in particular in rice crops (planted or sown under upland or paddy conditions using indica and/or japonica varieties and also hybrids/mutants/GMOs).

Compounds from the group of the pyrimidines are already known as herbicidally active compounds for controlling unwanted vegetation; see, for example GB 118623, U.S. Pat. No. 4,002,628, WO 200006553, U.S. Pat. No. 4,906,285, EP 658549, U.S. Pat. No. 5,118,339, WO 2002034724, WO 199105781, U.S. Pat. Nos. 4,932,999, 5,344,812, 3,325,357, 5,183,492, 3,235,360, 3,235,357, EP 1122244 and the literature cited in the publications mentioned above

DETAILED DESCRIPTION OF THE INVENTION

Accordingly, the present invention provides a herbicide combination comprising components (A) and (B) where
(A) denotes one or more compounds or salts thereof from the group described by the general formula (I):

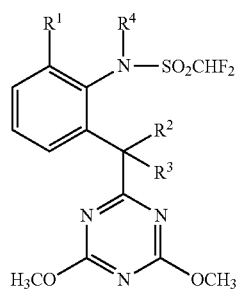

in which
R$^1$ is halogen, preferably fluorine or chlorine,
R$^2$ is hydrogen and R$^3$ is hydroxyl or
R$^2$ and R$^3$ together with the carbon atom to which they are attached are a carbonyl group C=O and
R$^4$ is hydrogen or methyl;
and
(B) denotes one or more herbicides from the group of the pyrimidines consisting of:
the subgroup of the pyrimidinylcarbinols (subgroup 1) consisting of:
(B1-1) ancymidol (PM #31), for example α-cyclopropyl-α-(4-methoxyphenyl)-5-pyrimidinemethanol (application rate: 1-5000 g of AS/ha, preferably 3-4000 g of AS/ha; weight ratio A:B=1:5000-500:1, preferably 1:800-70:1);
(B1-2) flurprimidol (PM #403), for example α-(1-methylethyl)-α-[4-(trifluoromethoxy)phenyl]-5-pyrimidinemethanol, also including its racemate or isomers (application rate: 1-5000 g of AS/ha, preferably 3-4000 g of AS/ha; weight ratio A:B=1:5000-500:1, preferably 1:800-70:1);
(B1-3) pyrimisulfan (CPCN), syn. KIH5996, for example N-[2-[(4,6-dimethoxy-2-pyrimidinyl)hydroxymethyl]-6-(methoxymethyl)phenyl]-1,1-difluoromethanesulfonamide, also including its salts (derivatives) (application rate: 1-500 g of AS/ha, preferably 3-400 g of AS/ha; weight ratio A:B=1:500-500:1, preferably 1:80-70:1);

the subgroup of the pyrimidinyloxybenzoic acid derivatives (subgroup 2), consisting of:
(B2-1) bispyribac-sodium (PM #85), for example sodium 2,6-bis[(4,6-dimethoxy-2-pyrimidinyl)oxy]benzoate (sodium salt), also including its acid (for example 2,6-bis(4,6-dimethoxypyrimidin-2-yloxy)benzoic acid) and other salts (derivatives) (application rate: 1-500 g of AS/ha, preferably 3-400 g of AS/ha; weight ratio A:B=1:500-500:1, preferably 1:80-70:1);
(B2-2) pyribenzoxim (PM #717), syn. SGC 40863, for example diphenylmethanone, O-[[2,6-bis(4,6-dimethoxy-2-pyrimidinyl)oxy]benzoyl]oxime (application rate: 1-500 g of AS/ha, preferably 3-400 g of AS/ha; weight ratio A:B=1:500-500:1, preferably 1:80-70:1);
(B2-3) pyriminobac-methyl (PM #727), syn. KIH 6127, for example methyl 2-[(4,6-dimethoxypyrimidin-2-yl)oxy]-6-[1-(methoxyimino)ethyl]benzoate (methyl ester), also including its acid pyriminobac (for example 2,6-bis(4,6-dimethoxypyrimidin-2-yloxy) benzoic acid) and its salts and other esters (derivatives) (application rate: 1-500 g of AS/ha, preferably 3-400 g of AS/ha; weight ratio A:B=1:500-500:1, preferably 1:80-70:1);
(B2-4) pyribambenz-isopropyl (published inter alia in WO2005/002338 A1), for example the isopropyl esters of pyrimidinyloxybenzylaminobenzoic acids, Chemical Abstract Service Registry Number [CAS RN 420138-41-6], also including the acid and other esters (derivatives) except for pyribambenz-propyl (application rate: 1-500 g of AS/ha, preferably 3-400 g of AS/ha; weight ratio A:B=1:500-500: 1, preferably 1:80-70:1);
(B2-5) pyribambenz-propyl (published inter alia in WO2005/002338 A1), for example the propyl esters of pyrimidinyloxybenzylaminobenzoic acids, Chemical Abstract Service Registry Number [CAS RN 420138-40-5] (application rate: 1-500 g of AS/ha, preferably 3-400 g of AS/ha; weight ratio A:B=1:500-500:1, preferably 1:80-70:1);
the subgroup of the pyrimidinylthiobenzoic acid derivatives (subgroup 3) consisting of:
(B3-1) pyriftalid (CPCN), for example (RS)-7-(4,6-dimethoxypyrimidin-2-ylthio)-3-methyl-2-benzofuran-1(3H)-one, also including its racemate or isomers (application rate: 3-2000 g of AS/ha, preferably 5-1500 g of AS/ha; weight ratio A:B=1:2000-100:1, preferably 1:300-40:1);
(B3-2) pyrithiobac-sodium (PM #729) for example sodium 2-chloro-6-(4,6-dimethoxypyrimidin-2-ylthio)benzoate (sodium salt), also including its acid (for example 2-chloro-6-(4,6-dimethoxypyrimidin-2-ylthio)benzoic acid) and other salts (derivatives) (application rate: 1-500 g of AS/ha, preferably 3-400 g of AS/ha; weight ratio A:B=1:500-500:1, preferably 1:80-70:1);
the subgroup of the pyrimidinediones (subgroup 4) consisting of:
(B4-1) benzfendizone (PM #70), for example methyl 2-[2-[[4-[3,6-dihydro-3-methyl-2,6-dioxo-4-(trifluoromethyl)-1(2H)-pyrimidinyl]phenoxy]methyl]-5-ethylphenoxy]propanoate (application rate: 10-5000 g of AS/ha, preferably 30-4000 g of AS/ha; weight ratio A:B=1:5000-50:1, preferably 1:800-7:1);
(B4-2) bromacil (PM #92), for example 5-bromo-6-methyl-3-(1-methylpropyl)-2,4(1H,3H)-pyrimidinedione), also including its salts, in particular the lithium salt (for example bromacil-lithium) (application rate: 10-5000 g of AS/ha, preferably 30-4000 g of AS/ha; weight ratio A:B=1:5000-50:1, preferably 1:800-7:1);

(B4-3) butafenacil (PM #103), for example 1,1-dimethyl-2-oxo-2-(2-propenyloxy)ethyl 2-chloro-5-[3,6-dihydro-3-methyl-2,6-dioxo-4-(trifluoromethyl)-1(2H)-pyrimidinyl]benzoate (application rate: 3-2000 g of AS/ha, preferably 5-1500 g of AS/ha; weight ratio A:B=1:2000-100:1, preferably 1:300-40:1);

(B4-4) lenacil (PM #504), for example 3-cyclohexyl-6,7-dihydro-1H-cyclopentapyrimidine-2,4(3H,5H)-dione (application rate: 10-5000 g of AS/ha, preferably 30-4000 g of AS/ha; weight ratio A:B=1:5000-50:1, preferably 1:800-7:1);

(B4-5) terbacil (PM #792), for example 5-chloro-3-(1,1-dimethylethyl)-6-methyl-2,4(1H,3H)-pyrimidinedione (application rate: 10-5000 g of AS/ha, preferably 30-4000 g of AS/ha; weight ratio A:B=1:5000-50:1, preferably 1:800-7:1);

(B4-6) SYN-523 (described in: EP 1122244; Eur. Chem. News, 82 (February 2005), p. 27; Farm Chemicals Int. (April 2005), 19 (3), 6; AGROW 2005-02-14.), for example ethyl [[3-[2-chloro-5-[3,6-dihydro-3-methyl-2,6-dioxo-4-(trifluoromethyl)-1(2H)-pyrimidinyl]-4-fluorophenoxy]-2-pyridinyl]oxy]acetate; Chemical Abstract Service Registry Number [CAS RN 353292-31-6], also including its acid and other esters and salts (derivatives) (application rate: 1-1000 g of AS/ha, preferably 2-800 g of AS/ha; weight ratio A:B=1:1000-250:1, preferably 1:160-100:1);

(B4-7) saflufenacil (CPCN), syn. BAS H800, for example 2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide; Chemical Abstract Service Registry Number [CAS RN 372137-35-4] (application rate: 1-1000 g of AS/ha, preferably 2-800 g of AS/ha; weight ratio A:B=1:1000-250:1, preferably 1:160-100:1);

except for the following combinations which are described in PCT/EP2008/000870 (unpublished):

compounds of the general formula (I) where $R^1$ is fluorine, $R^2$ and $R^3$ are a carbonyl group C=O, $R^4$ is methyl, and the compound B1-3 (pyrimisulfan);

The compounds mentioned above in group B are referred to either by the "common name" according to the International Organization for Standardization (ISO) or by the chemical name or by a code number (development code); as known, for example, from the following sources "The Pesticide Manual", 14$^{th}$ edition 2006/2007 or "The e-Pesticide Manual", version 4.0 (2006-07), each published by the British Crop Protection Council (abbreviation: "PM #.." with the respective sequential entry number, and the literature cited therein, from "The Compendium of Pesticide Common Names" (abbreviation: "CPCN"; internet URL: http://www.alanwood.net/pesticides/) and/or other sources. The use of the names mentioned above, for example in the short form of the "common names", includes in each case all use forms (derivatives) such as acids, salts, esters and isomers such as stereoisomers and optical isomers, unless not already more specifically defined. The commercial use forms of the herbicides mentioned in group B are preferred. Here, the abbreviation "AS/ha" above means "active substance per hectare" and is based on 100% pure active compound.

Preferred components (A) are the following compounds (A-1) to (A-8) of the formulae (A1), (A2), (A3), (A4), (A5), (A6), (A7) and (A8) or their salts:

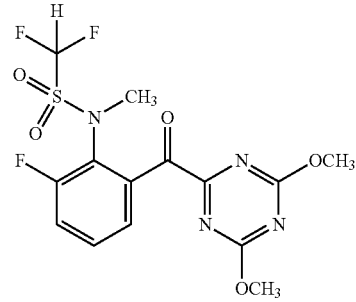
(A1)

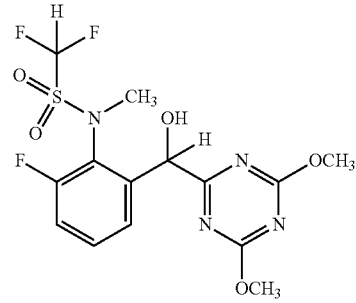
(A2)

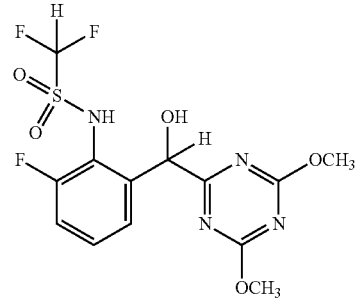
(A3)

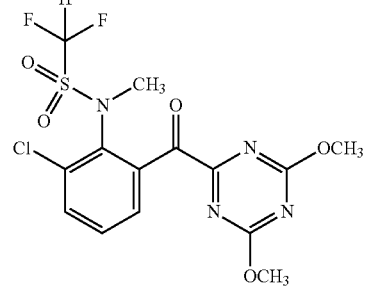
(A4)

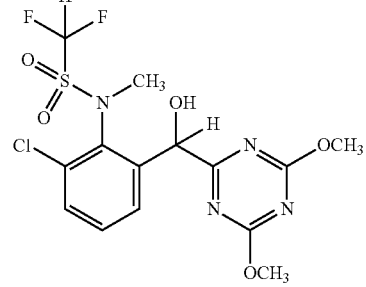
(A5)

(A6)

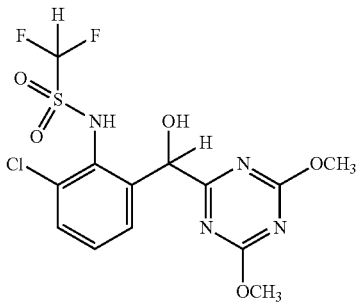

(A7)

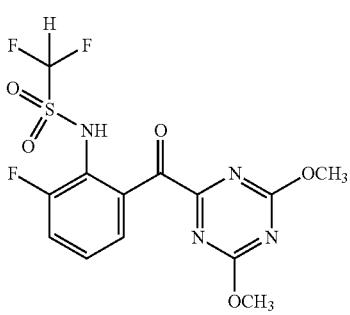

(A8)

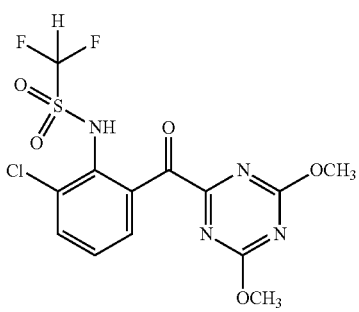

Particularly preferred as components (A) are the compounds (A-1), (A-2) and (A-3).

Compounds preferred as components (B) are:
(B1-3) pyrimisulfan, (B2-1) bispyribac-sodium, (B3-1) pyriftalid, (B3-2) pyrithiobac-sodium, (B4-2) bromacil, (B4-6) SYN-523, (B4-7) saflufenacil; particularly preferably (B1-3) pyrimisulfan, (B2-1) bispyribac-sodium, (B4-6) SYN-523, (B4-7) saflufenacil.

The herbicide combinations according to the invention may additionally comprise further components: for example agrochemically active compounds of a different type and/or formulation auxiliaries and/or additives customary in crop protection, or they may be employed together with these. Hereinbelow, the use of the term "herbicide combination(s)" or "combination(s)" also includes the "herbicidal compositions" formed in this manner.

The compounds of the formula (I) are capable of forming salts. The salt formation may take place by allowing a base to act on those compounds of the formula (I) carrying an acidic hydrogen atom. Suitable bases are, for example, organic amines, such as trialkylamines, morpholine, piperidine or pyridine, and also ammonium, alkali metal or alkaline earth metal hydroxides, carbonates and bicarbonates, in particular sodium hydroxide and potassium hydroxide, sodium carbonate and potassium carbonate and sodium bicarbonate and potassium bicarbonate, alkali metal or alkaline earth metal alkoxides, in particular sodium methoxide, ethoxide, n-propoxide, isopropoxide, n-butoxide or t-butoxide or potassium methoxide, ethoxide, n-propoxide, isopropoxide, n-butoxide or t-butoxide. These salts are compounds in which the acidic hydrogen is replaced by an agriculturally suitable cation, for example metal salts, in particular alkali metal salts or alkaline earth metal salts, especially sodium salts or potassium salts, or else ammonium salts, salts with organic amines or quaternary ammonium salts, for example with cations of the formula $[NRR'R''R''']^+$ in which R to R''' are in each case independently of one another organic radicals, in particular alkyl, aryl, arylalkyl or alkylaryl. Also suitable are alkylsulfonium and alkylsulfoxonium salts, such as $(C_1-C_4)$-trialkylsulfonium and $(C_1-C_4)$-trialkylsulfoxonium salts. By a suitable inorganic or organic acid, such as, for example, mineral acids such as, for example, HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, such as, for example, p-toluenesulfonic acid, forming an adduct with a basic group such as, for example, amino, alkylamino, dialkylamino, piperidino, morpholino or pyridino, the compounds of the formula (I) are also capable of forming salts. These salts then contain the conjugated base of the acid as anion.

Hereinbelow, the terms "herbicide(s)", "individual herbicide(s)", "compound(s)" or "active compound(s)" are also used synonymously for the term "components(s)" in the context. In a preferred embodiment, the herbicide combinations according to the invention comprise effective amounts of the herbicides (A) and (B) and/or have synergistic actions. The synergistic actions can be observed, for example, when applying the herbicides (A) and (B) together, for example as a coformulation or as a tank mix; however, they can also be observed when the active compounds are applied at different times (splitting). It is also possible to apply the herbicides or the herbicide combinations in a plurality of portions (sequential application), for example pre-emergence applications followed by post-emergence applications or early post-emergence applications followed by medium or late post-emergence applications. Preference is given here to the joint or almost simultaneous application of the herbicides (A) and (B) of the combination in question, and the joint application is particularly preferred.

The synergistic effects permit a reduction of the application rates of the individual herbicides, a higher efficacy at the same application rate, the control of species which were as yet uncontrolled (gaps), control of species which are tolerant or resistant to individual herbicides or to a number of herbicides, an extension of the period of application and/or a reduction in the number of individual applications required and—as a result for the user—weed control systems which are more advantageous economically and ecologically.

For example, the combinations according to the invention of herbicides (A)+(B) allow the activity to be enhanced synergistically in a manner which, by far and in an unexpected manner, exceeds the activities which can be achieved using the individual herbicides (A) and (B).

The formula (I) mentioned embraces all stereoisomers and their mixtures, in particular also racemic mixtures, and—if enantiomers are possible—the respective enantiomer which is biologically active. This also applies to possible rotamers of the formula (I).

The herbicides of group (A) inhibit mainly the enzyme acetolactate synthase (ALS) and thus the protein biosynthesis in plants. The application rate of the herbicides (A) can vary within a wide range, for example between 0.1 g and 1000 g of AS/ha (hereinbelow, AS/ha means "active substance per hectare"=based on 100% pure active compound). Applied at application rates of from 0.1 g to 1000 g of AS/ha, the herbicides (A), preferably the compounds (A-1) to (A-8), control, when used in the pre-sowing pre-planting or the pre- and post-emergence method, a relatively wide spectrum of harmful plants, for example of annual and perennial mono- or dicotyledonous broad-leaved weeds, weed grasses and Cyperaceae, and also of unwanted crop plants. For the combinations according to the invention, the application rates are generally lower, for example in the range of from 0.1 g to 500 g of AS/ha, preferably from 0.5 g to 200 g of AS/ha, particularly preferably from 1 g to 150 g of AS/ha.

The herbicides of group (B) have an effect, for example, on acetohydroxy acid synthase, photosystem Il and protoporphyrinogen oxidase, and they are suitable both for pre-emergence and post-emergence application. The application rate of the herbicides (B) can vary within a wide range, for example between 1 g and 5,000 g of AS/ha (hereinbelow, AS/ha means "active substance per hectare"=based on 100% pure active compound). Applied at application rates of from 3 g to 4000 g of AS/ha, the herbicides (B), preferably the compounds (B1-3), (B2-1), (B3-1), (B3-2), (B4-2), (B4-6), and (B4-7), control, when used in the pre- and post-emergence method, a relatively wide spectrum of harmful plants, for example of annual and perennial mono- or dicotyledonous broad-leaved weeds, weed grasses and Cyperaceae, and also of unwanted crop plants. For the combinations according to the invention, the application rates are generally lower, for example in the range of from 1 g to 5000 g of AS/ha, preferably from 3 g to 4000 g of AS/ha, particularly preferably from 1 g to 3000 g of AS/ha.

Preference is given to herbicide combinations of one or more herbicides (A) and one or more herbicides (B). More preference is given to combinations of herbicides (A) with one or more herbicides (B). Here, combinations additionally comprising one or more further agrochemically active compounds which differ from the herbicides (A) and (B) but also act as selective herbicides are likewise in accordance with the invention.

For combinations of three or more active compounds, the preferred conditions illustrated below in particular for two-component combinations according to the invention primarily also apply, provided they comprise the two-component combinations according to the invention.

Ranges of suitable ratios of the compounds (A) and (B) can be found, for example, by looking at the application rates mentioned for the individual compounds. In the combinations according to the invention, the application rates can generally be reduced. Preferred mixing ratios of the combined herbicides (A):(B) in the combinations according to the invention are characterized by the following weight ratios: The weight ratio (A):(B) of the components (A) and (B) is generally in the range of from 1:5000 to 500:1, preferably 1:800 to 70:1, in particular 1:500 to 50:1.

Of particular interest is the use of herbicide combinations having a content of the following compounds (A)+(B):

(A-1)+(B1-1), (A-1)+(B1-2), (A-1)+(B1-3), (A-1)+(B2-1), (A-1)+(B2-2), (A-1)+(B2-3), (A-1)+(B2-4), (A-1)+(B2-5), (A-1)+(B3-1), (A-1)+(B3-2), (A-1)+(B4-1), (A-1)+(B4-2), (A-1)+(B4-3), (A-1)+(B4-4), (A-1)+(B4-5), (A-1)+(B4-6), (A-1)+(B4-7);

(A-2)+(B1-1), (A-2)+(B1-2), (A-2)+(B1-3), (A-2)+(B2-1), (A-2)+(B2-2), (A-2)+(B2-3), (A-2)+(B2-4), (A-2)+(B2-5), (A-2)+(B3-1), (A-2)+(B3-2), (A-2)+(B4-1), (A-2)+(B4-2), (A-2)+(B4-3), (A-2)+(B4-4), (A-2)+(B4-5), (A-2)+(B4-6), (A-2)+(B4-7);

(A-3)+(81-1), (A-3)+(B1-2), (A-3)+(B1-3), (A-3)+(B2-1), (A-3)+(B2-2), (A-3)+(B2-3), (A-3)+(B2-4), (A-3)+(B2-5), (A-3)+(B3-1), (A-3)+(B3-2), (A-3)+(B4-1), (A-3)+(B4-2), (A-3)+(B4-3), (A-3)+(B4-4), (A-3)+(B4-5), (A-3)+(B4-6), (A-3)+(B4-7);

(A-4)+(B1-1), (A-4)+(B1-2), (A-4)+(B1-3), (A-4)+(B2-1), (A-4)+(B2-2), (A-4)+(B2-3), (A-4)+(B2-4), (A-4)+(B2-5), (A-4)+(B3-1), (A-4)+(B3-2), (A-4)+(B4-1), (A-4)+(B4-2), (A-4)+(B4-3), (A-4)+(B4-4), (A-4)+(B4-5), (A-4)+(B4-6), (A-4)+(84-7);

(A-5)+(B1-1), (A-5)+(B1-2), (A-5)+(B1-3), (A-5)+(B2-1), (A-5)+(2-2), (A-5)+(B2-3), (A-5)+(B2-4), (A-5)+(B2-5), (A-5)+(B3-1), (A-5)+(B3-2), (A-5)+(84-1), (A-5)+(B4-2), (A-5)+(84-3), (A-5)+(B4-4), (A-5)+(B4-5), (A-5)+(B4-6), (A-5)+(B4-7);

(A-6)+(B1-1), (A-6)+(B1-2), (A-6)+(B1-3), (A-6)+(B2-1), (A-6)+(B2-2), (A-6)+(B2-3), (A-6)+(B2-4), (A-6)+(B2-5), (A-6)+(B3-1), (A-6)+(B3-2), (A-6)+(84-1), (A-6)+(B4-2), (A-6)+(B4-3), (A-6)+(B4-4), (A-6)+(B4-5), (A-6)+(B4-6), (A-6)+(B4-7);

(A-7)+(B1-1), (A-7)+(81-2), (A-7)+(81-3), (A-7)+(B2-1), (A-7)+(B2-2), (A-7)+(B2-3), (A-7)+(B2-4), (A-7)+(B2-5), (A-7)+(B3-1), (A-7)+(B3-2), (A-7)+(84-1), (A-7)+(B4-2), (A-7)+(B4-3), (A-7)+(B4-4), (A-7)+(B4-5), (A-7)+(B4-6), (A-7)+(84-7);

(A-8)+(B1-1), (A-8)+(B1-2), (A-8)+(B1-3), (A-8)+(B2-1), (A-8)+(B2-2), (A-8)+(B2-3), (A-8)+(B2-4), (A-8)+(B2-5), (A-8)+(B3-1), (A-8)+(B3-2), (A-8)+(B4-1), (A-8)+(B4-2), (A-8)+(B4-3), (A-8)+(B4-4), (A-8)+(B4-5), (A-8)+(B4-6), (A-8)+(B4-7);

The herbicide combinations according to the invention may furthermore comprise, as additional further components, various agrochemically active compounds, for example from the group of the safeners, fungicides, insecticides, acaricides, nematicides, bird repellants, soil structure improvers, plant nutrients (fertilizers), and herbicides which differ structurally from herbicides (A) and (B), and plant growth regulators, or from the group of the formulation auxiliaries and additives customary in crop protection.

Thus, suitable further herbicides are, for example, the following herbicides which differ structurally from the herbicides (A) and (B), preferably herbicidally active compounds whose action is based on inhibition of, for example, acetolactate synthase, acetyl coenzyme A carboxylase, cellulose synthase, enolpyruvylshikimate 3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or "The Pesticide Manual", 13$^{th}$ edition 2003 or 14$^{th}$ edition 2006/2007, or in the corresponding "The e-Pesticide Manual", version 4.0 (2006-07), all published by the British Crop Protection Council, and the literature cited therein, can be used. Lists of common names are also available in "The Compendium of Pesticide Common Names" on the internet. Here, the herbicides are referred to either by the "common name" in accordance with the International Organization for Standardization (ISO) or by the chemical name or by the code number, and in each case include all use forms, such as acids, salts, esters and isomers, such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammoniumsulfamat, anilofos, asulam, atrazine, azafenidin, azimsulfuron, aziprotryn, BAH-043, BAS-140H, BAS-693H, BAS-714H, BAS-762H, BAS-776H, beflubutamid, benazolin, benazolin-ethyl, bencarbazone, benfluralin, benfuresate, bensulide, bensulfuron-methyl, bentazone, benzobicyclon, benzofenap, benzofluor, benzoylprop, bifenox, bilanafos, bilanafos-sodium, bromobutide, bromofenoxim, bromoxynil, bromuron, buminafos, busoxinone, butachlor, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, KUH-071, karbutilate, ketospiradox, lactofen, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyributicarb, pyridafol, pyridate, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-449, SYP-249, SYP-298, SYP-300, tebutam, tebuthiuron, tecnazene, tefuryltrione, tembotrione, tepraloxydim, terbucarb, terbuchlor, terbumeton, terbuthylazine, terbutryn, TH-547, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

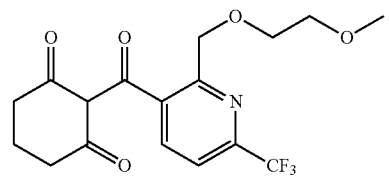

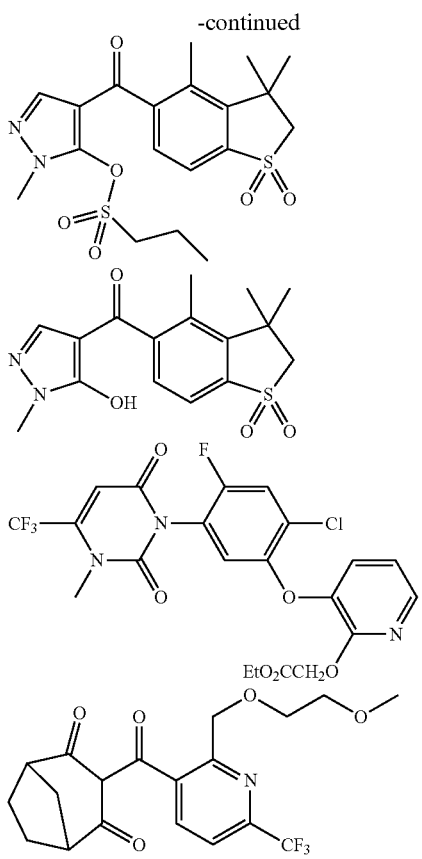

Of particular interest is the selective control of harmful plants in crops of useful plants and ornamental plants. Although the herbicides (A) and (B) have already demonstrated very good to sufficient selectivity in a large number of crops, in principle, in some crops and in particular also in the case of mixtures with other, less selective herbicides, phytotoxicities on the crop plants may occur. In this respect, combinations of herbicides (A) and (B) comprising the herbicidally active compounds combined according to the invention and one or more safeners are of particular interest. The safeners, which are used in an antidotically effective amount, reduce the phytotoxic side effects of the herbicides/pesticides employed, for example in economically important crops, such as cereals (wheat, barley, rye, oats, corn, rice, millet), sugar beet, sugar cane, oilseed rape, cotton, soybeans or in fruit plantations (plantation crops), preferably cereals, in particular rice.

The following groups of compounds are, for example, suitable as safeners (including possible stereoisomers and agriculturally customary esters or salts):
benoxacor
cloquintocet (-mexyl)
cyometrinil
cyprosulfamide
dichlormid
dicyclonon
dietholate
disulfoton (=O,O-diethyl S-2-ethylthioethyl phosphordithioate)
fenchlorazole (-ethyl)
fenclorim
flurazole
fluxofenim
furilazole
isoxadifen (-ethyl)
mefenpyr (-diethyl)
mephenate
naphthalic anhydride
oxabetrinil
"R-29148" (=3-dichloroacetyl-2,2,5-trimethyl-1,3-oxazolidine),
"R-28725" (=3-dichloroacetyl-2,2-dimethyl-1,3-oxazolidine),
"PPG-1292" (=N-allyl-N-[(1,3-dioxolan-2-yl)methyl] dichloroacetamide),
"DKA-24" (=N-allyl-N-[(allylaminocarbonyl)methyl] dichloroacetamide),
"AD-67" or "MON 4660" (=3-dichloroacetyl-1-oxa-3-azaspiro[4,5]decane),
"TI-35" (=1-dichloroacetylazepane),
"dimepiperate" or "MY-93" (=S-1-methyl-1-phenylethyl piperidine-1-thiocarboxylate),
"daimuron" or "SK 23" (=1-(1-methyl-1-phenylethyl)-3-p-tolylurea),
"cumyluron" ="JC-940" (=3-(2-chlorophenylmethyl)-1-(1-methyl-1-phenylethyl)urea),
"methoxyphenon" or "NK 049" (=3,3'-dimethyl-4-methoxybenzophenone),
"CSB" (=1-bromo-4-(chloromethylsulfonyl)benzene)
"CL-304415" (=4-carboxy-3,4-dihydro-2H-1-benzopyran-4-acetic acid; CAS reg no: 31541-57-8)
"MG-191" (=2-dichloromethyl-2-methyl-1,3-dioxolane)
"MG-838" (=2-propenyl 1-oxa-4-azaspiro[4.5]decane-4-carbodithioate; CAS reg no: 133993-74-5)
methyl(diphenylmethoxy)acetate (CAS reg no: 41858-19-9 from WO-A-1998/38856)
methyl[(3-oxo-1H-2-benzothiopyran-4(3H)-ylidene)methoxy]acetate (CAS reg no: 205121-04-6 from WO-A-1998/13361)
1,2-dihydro-4-hydroxy-1-methyl-3-(5-tetrazolylcarbonyl)-2-quinolone (CAS reg no: 95855-00-8 from WO-A-1999/000020).

Some of the safeners are already known as herbicides and accordingly, in addition to the herbicidal action against harmful plants, also act by protecting the crop plants.

The weight ratios of herbicide combination to safener generally depend on the herbicide application rate and the effectiveness of the safener in question and may vary within wide limits, for example in the range from 90 000:1 to 1:5000, preferably from 7000:1 to 1:1600, in particular from 3000:1 to 1:500. The safeners may be formulated analogously to the compounds of the formula (I) or their mixtures with other herbicides/pesticides and be provided and used as a finished formulation or as a tank mix with the herbicides or separately be applied as a seed, soil or foliar application.

The herbicide combinations according to the invention (=herbicidal compositions) have excellent herbicidal activity against a broad spectrum of economically important monocotyledonous and dicotyledonous harmful plants, such as broad-leaved weeds, weed grasses or Cyperaceae, including species which are resistant to herbicidally active compounds such as glyphosate, glufosinate, atrazine, imidazolinone herbicides, sulfonylureas, (hetero)aryloxyaryloxyalkylcarboxylic acids or -phenoxyalkylcarboxylic acids ('fops'), cyclohexanedione oximes ('dims') or auxin inhibitors. The active compounds also act efficiently on perennial weeds which produce shoots from rhizomes, root stocks and other perennial organs and which are difficult to control. Here, the substances can be applied, for example, by the pre-sowing method, the pre-emergence method or the post-emergence method, for example jointly or separately. Preference is given, for example, to application by the post-emergence method, in particular to the emerged harmful plants.

Specific examples may be mentioned of some representatives of the monocotyledonous and dicotyledonous weed flora which can be controlled by the compounds according to the invention, without the enumeration being restricted to certain species.

Examples of weed species on which the herbicidal compositions act efficiently are, from amongst the monocotyledonous weed species, *Avena* spp., *Alopecurus* spp., *Apera* spp., *Brachiaria* spp., *Bromus* spp., *Digitaria* spp., *Lolium* spp., *Echinochloa* spp., *Leptochloa* spp., *Fimbristylis* spp., *Panicum* spp., *Phalaris* spp., *Poa* spp., *Setaria* spp. and also *Cyperus* species from the annual group, and, among the perennial species, *Agropyron, Cynodon, Imperata* and *Sorghum* and also perennial *Cyperus* species.

In the case of the dicotyledonous weed species, the spectrum of action extends to genera such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. *Eclipta* spp., *Sesbania* spp., *Aeschynomene* spp. and *Viola* spp., *Xanthium* spp. among the annuals, and *Convolvulus, Cirsium, Rumex* and *Artemisia* in the case of the perennial weeds.

If the active compounds of the herbicide combinations according to the invention are applied to the soil surface before germination, the weed seedlings are either prevented completely from emerging or else the weeds grow until they have reached the cotyledon stage, but then their growth stops, and, eventually, after two to four weeks have elapsed, they die completely.

If the active compounds are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner. In the case of rice, the active compounds can also be applied into the water, and they are then taken up via soil, shoot and roots.

The herbicidal compositions according to the invention are distinguished by a rapidly commencing and long-lasting herbicidal action. As a rule, the rainfastness of the active compounds in the combinations according to the invention is favorable. A particular advantage is that the dosages used in the combinations and the effective dosages of compounds (A) and (B) can be adjusted to such a low level that their soil action is optimally low. This does not only allow them to be employed in sensitive crops in the first place, but ground water contaminations are virtually avoided. The combinations according to the invention of active compounds allow the required application rate of the active compounds to be reduced considerably.

In a preferred embodiment, the herbicide combinations according to the invention of the herbicides (A) and (B) are highly suitable for the selective control of harmful plants in rice crops. These include all possible forms of rice cultivation under the most diverse conditions, such as upland cultivation, dry cultivation or paddy cultivation, where the irrigation may be natural (rainfall) and/or artificial (irrigated, flooded). The rice used for this purpose may be conventionally cultivated seed, hybrid seed, or else resistant, at least tolerant, seed (obtained by mutagenesis or transgenically) which can be derived from the indica or japonica variety or from crossbreeds thereof.

The herbicide combinations according to the invention can be applied by all application methods customary for rice herbicides. Particularly preferably, they are applied by spray application and/or by submerged application. In the submerged application, the paddy water already covers the ground by up to 3-20 cm at the time of the application. The herbicide combinations according to the invention are then directly placed in the paddy water, for example in the form of granules. Worldwide, the spray application is used predominantly with direct seeded rice and the submerged application is used predominantly with transplanted rice.

The herbicide combinations according to the invention cover a broad weed spectrum which is specific in particular for rice crops. From among the monocotyledonous weeds, genera such as, for example, *Echinochloa* spp., *Panicum* spp., *Poa* spp., *Leptochloa* spp., *Brachiaria* spp., *Digitaria* spp., *Setaria* spp. *Cyperus* spp., *Monochoria* spp., *Fimbristylis* spp., *Sagittaria* spp., *Eleocharis* spp., *Scirpus* spp., *Alisma* spp., *Aneilema* spp., *Blyxa* spp., *Eriocaulon* spp., *Potamogeton* spp. and the like are controlled well, in particular the species *Echinochloa oryzicola, Monochoria vaginalis, Eleocharis acicularis, Eleocharis kuroguwai, Cyperus difformis, Cyperus serotinus, Sagittaria pygmaea, Alisma canaliculatum, Scirpus juncoides*. In the case of the dicotyledonous weeds, the activity spectrum extends to genera such as, for example, *Polygonum* spp., *Rorippa* spp., *Rotala* spp., *Lindernia* spp., *Bidens* spp., *Sphenoclea* spp., *Dopatrium* spp., *Eclipta* spp., *Elatine* spp., *Gratiola* spp., *Lindernia* spp., *Ludwigia* spp., *Oenanthe* spp., *Ranunculus* spp., *Deinostema* spp. and the like. In particular species such as *Rotala indica, Sphenoclea zeylanica, Lindernia procumbens, Ludwigia prostrate, Potamogeton distinctus, Elatine triandra, Oenanthe javanica* are controlled well.

When herbicides of group (A) and those of group (B) are applied jointly, there are preferably superadditive (=synergistic) effects. Here, the activity in the combinations is higher than the expected sum of the activities of the individual herbicides employed. The synergistic effects allow the application rate to be reduced, a broader spectrum of broad-leaved weeds, weed grasses and Cyperaceae to be controlled, a more rapid onset of the herbicidal action, a longer persistency, a better control of the harmful plants with only one or a few applications and a widening of the application period possible. To some extent, by using the compositions, the amount of harmful ingredients, such as nitrogen or oleic acid, and their introduction into the soil are likewise reduced.

The abovementioned properties and advantages are necessary for weed control practice to keep agricultural/forestry/horticultural crops or green land/meadows free of unwanted competing plants, and thus to ensure and/or increase yield levels from the qualitative and quantitative angle. These novel herbicide combinations markedly exceed the technical state of the art with a view to the properties described.

Owing to their herbicidal and plant growth-regulatory properties, the herbicide combinations according to the invention can be employed for controlling harmful plants in known plant crops or in tolerant or genetically modified crop and energy plants still to be developed. In general, the transgenic plants (GMOs) are distinguished by specific advantageous properties, in addition to resistances to the herbicide combinations according to the invention, for example, by resistances to plant diseases or the causative organisms of plant diseases such as certain insects or microorganisms, such as fungi, bacteria or viruses. Other specific characteristics relate, for example, to the harvested material with regard to quantity, quality, storability, and the composition of specific constituents. Thus, transgenic plants are known whose starch content is increased, or whose starch quality is altered, or those where the harvested material has a different fatty acid composition, or increased vitamin content or energetic properties. In the same manner, owing to their herbicidal and plant growth-regulatory properties, the active compounds can also be used for controlling harmful plants in crops of known plants or plants still to be developed by mutant selection, and also crossbreeds of mutagenic and transgenic plants.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit resistances to herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated; see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene and Klone", VCH Weinheim $2^{nd}$ Edition 1996 or Christou, "Trends in Plant Science" 1 (1996) 423-431). To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to entire plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The present invention furthermore provides a method for the selective control of unwanted plants, preferably in crop plants, in particular in rice crops (planted or sown under upland or paddy conditions using indica and/or japonica species and/or hybrids/mutants/GMOs), which comprises applying the herbicides as components (A) and (B) of the herbicide combinations according to the invention to the plants (for example harmful plants, such as monocotyledonous or dicotyledonous broad-leaved weeds, weed grasses, Cyperaceae or unwanted crop plants), the seed (for example grains, seeds or vegetative propagation organs, such as tubers or shoot parts with buds) or to the area in which the plants grow (for example the area under cultivation, which may also be covered by water), for example together or separately. One or more herbicides (A) may be applied before, after or simultaneously with the herbicide(s) (B) to the plants, the seed or the area in which the plants grow (for example the area under cultivation).

Unwanted plants are to be understood as meaning all plants which grow in locations where they are unwanted. These can, for example, be harmful plants (for example monocotyledonous or dicotyledonous weeds, weed grasses, Cyperaceae or unwanted crop plants), including, for example, those which are resistant to certain herbicidally active compounds, such as glyphosate, glufosinate, atrazine, imidazolinone herbicides, sulfonylureas, (hetero)aryloxyaryloxyalkylcarboxylic acids or -phenoxyalkylcarboxylic acids ('fops'), cyclohexanedione oximes ('dims') or auxin inhibitors.

The herbicide combinations according to the invention are employed selectively for controlling unwanted vegetation, for example in crop plants such as farm crops, for example monocotyledonous farm crops, such as cereals (for example wheat, barley, rye, oats, rice, corn, millet), or dicotyledonous farm crops, such as sugar beet, sugar case, oilseed rape, cotton, sunflowers and leguminous plants, for example of the genera *Glycine* (for example *Glycine max.* (soybean), such as non-transgenic *Glycine max.* (for example conventional cultivars, such as STS cultivars) or transgenic *Glycine max.* (for example RR-soybean or LL-soybean) and crossbreeds thereof), *Phaseolus, Pisum, Vicia* and *Arachis*, or vegetable crops from various botanical groups, such as potato, leek, cabbage, carrot, tomato, onion, in fruit plantations (plantation crops), greens, lawns and pasture areas, or on non-crop areas (for example squares of residential areas or industrial sites, rail tracks) in particular in rice crops (planted or sown under upland or paddy conditions using indica or japonica varieties and also hybrids/mutants/GMOs). The application is preferably carried out both prior to the emergence of the harmful plants and to the emerged harmful plants (for example broad-leaved weeds, weed grasses, Cyperaceae or unwanted crop plants), independently of the stage of the sown/planted crop.

The invention also provides the use of the herbicide combinations according to the invention for selectively controlling unwanted vegetation, preferably in crop plants, in particular in rice crops (planted or sown under upland or paddy conditions using indica or japonica varieties and also hybrids/mutants/GMOs).

The herbicide combinations according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components. It is also possible to use the herbicides or the herbicide combinations in a plurality of portions (sequential application), for example after application as seed dressing or pre-sowing/planting treatment or pre-emergence applications followed by post-emergence applications or early post-emergence applications followed by medium or late post-emergence applications. Preference is given here to the joint or almost simultaneous use of the active compounds of the combination in question, and the joint use is particularly preferred.

The herbicides (A) and (B) can be converted jointly or separately into customary formulations, such as solutions, emulsions, suspensions, powders, foams, pastes, granules, aerosols, natural and synthetic materials impregnated with active compound and microencapsulations in polymeric materials. Mention may also be made of formulations specific for the cultivation of rice, such as, for example, granules for scattering, jumbo granules, floating granules, floating suspoemulsions applied via shaker bottles and dissolved in and distributed via the paddy water. The formulations may comprise the customary auxiliaries and additives.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

Suitable solid carriers are: for example ammonium salts and ground natural minerals such as kaolins, clays, talc, chalk, quartz, attapulgite, montmorillonite or diatomaceous earth, and ground synthetic minerals such as highly-disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkyl sulfonates, alkyl sulfates, aryl sulfonates, and also protein hydrolysates; suitable dispersants are: for example lignosulphite waste liquors and methyl cellulose.

Tackifiers, such as carboxymethyl cellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

The herbicidal action of the herbicide combinations according to the invention can be improved, for example, by surfactants, preferably by wetting agents from the group of the fatty alcohol polyglycol ethers. The fatty alcohol polyglycol ethers preferably comprise 10-18 carbon atoms in the fatty alcohol radical and 2-20 ethylene oxide units in the polyglycol ether moiety. The fatty alcohol polyglycol ethers may be present in nonionic form, or ionic form, for example in the form of fatty alcohol polyglycol ether sulfates, which may be used, for example, as alkali metal salts (for example sodium salts and potassium salts) or ammonium salts, or even as alkaline earth metal salts, such as magnesium salts, such as $C_{12}/C_{14}$-fatty alcohol diglycol ether sulfate sodium (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, ($C_{10}$-$C_{18}$)-, preferably ($C_{10}$-$C_{14}$)-fatty alcohol polyglycol ethers (for example isotridecyl alcohol polyglycol ethers) which comprise, for example, 2-20, preferably 3-15, ethylene oxide units, for example those from the Genapol® X-series, such as Genapol® X-030, Genapol® X-060, Genapol® X-080 or Genapol® X-150 (all from Clariant GmbH).

The present invention further comprises the combination of components (A) and (B) with the wetting agents mentioned above from the group of the fatty alcohol polyglycol ethers which preferably contain 10-18 carbon atoms in the fatty alcohol radical and 2-20 ethylene oxide units in the polyglycol ether moiety and which may be present in nonionic or ionic form (for example as fatty alcohol polyglycol ether sulfates). Preference is given to $C_u/C_u$-fatty alcohol diglycol ether sulfate sodium (Genapol® LRO, Clariant GmbH) and isotridecyl alcohol polyglycol ether having 3-15 ethylene oxide units, for example from the Genapol® X-series, such as Genapol® X-030, Genapol® X-060, Genapol® X-080 and Genapol® X-150 (all from Clariant GmbH).

Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014). Accordingly, the present invention also embraces the combination with suitable penetrants and activity enhancers, preferably in commercially available form.

The herbicide combinations according to the invention can also be used together with vegetable oils. The term vegetable oils is to be understood as meaning oils of oleaginous plant species, such as soybean oil, rapeseed oil, corn oil, sunflower oil, cottonseed oil, linseed oil, coconut oil, palm oil, thistle oil or castor oil, in particular rapeseed oil, and also their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid and in particular $C_{18}$-fatty acids, such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids contained, for example, in oils of oleaginous plant species, or $C_1$-$C_{20}$-alkyl-$C_{10}$-$C_{22}$-fatty acid esters which can be obtained, for example, by transesterification of the aforementioned glycerol- or glycol-$C_{10}$-$C_{22}$-fatty acid esters with $C_1$-$C_{20}$-alcohols (for example methanol, ethanol, propanol or butanol). The transesterification can be carried out by known methods as described, for example, in Römpp Chemie Lexikon, 9th edition, Volume 2, page 1343, Thieme Verlag Stuttgart. Preferred $C_1$-$C_{20}$-alkyl-$C_{10}$-$C_{22}$-fatty acid esters are methyl esters, ethyl esters, propyl esters, butyl esters, 2-ethylhexyl esters and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular fatty acids having an even number of carbon atoms, for example erucic acid, lauric acid, palmitic acid and, in particular, $C_{18}$-fatty acids, such as stearic acid, oleic acid, linoleic acid or linolenic acid.

In the herbicidal compositions according to the invention, the vegetable oils can be present, for example, in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob® B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

In a further embodiment, the present invention also comprises combinations with the vegetable oils mentioned above, such as rapeseed oil, preferably in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

In general, the formulations comprise between 0.1 and 95% by weight of active compound, preferably between 0.5 and 90% by weight.

As such or in their formulations, the herbicides (A) and (B) can also be used as a mixture with other agrochemically active compounds, such as known herbicides, for controlling unwanted vegetation, for example for controlling weeds or for controlling unwanted crop plants, finished formulations or tank mixes, for example, being possible.

Mixtures with other known active compounds, such as fungicides, insecticides, acaricides, nematicides, safeners, bird repellents, plant nutrients and agents which improve soil structure, are also possible.

The herbicides (A) and (B) can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds can be applied to the plants (for example harmful plants, such as monocotyledonous or dicotyledonous broad-leaved weeds, weed grasses, Cyperaceae or unwanted crop plants), the seed (for example grains, seeds or vegetative propagation organs, such as tubers or shoot parts with buds) or the area under cultivation (for example the soil), preferably to the green plants and parts of plants and, if appropriate, additionally the soil. One possible use is the joint application of the active compounds in the form of tank mixes, where the optimally formulated concentrated formulations of the individual active compounds are, together, mixed in a tank with water, and the spray liquor obtained is applied.

A joint herbicidal formulation of the combination according to the invention of herbicides (A) and (B) has the advantage that it is easier to apply, since the amounts of the components are already in an optimum ratio. Moreover, the auxiliaries in the formulation can be adjusted optimally to one another.

BIOLOGICAL EXAMPLES

Post-emergence Action Against Weeds

Method

Seeds or rhizome pieces of mono- and dicotyledonous harmful and useful plants were placed in peat pots (diameter 4 cm) filled with sandy loam and then covered with soil. The pots were kept in a greenhouse under optimum conditions. In addition, harmful plants encountered in paddy rice cultivation were cultivated in pots with a water level 2 cm above the soil surface.

About three weeks after the start of the cultivation, the test plants were treated at the 2- to 3-leaf stage. The herbicides, formulated as powder or liquid concentrates, were, either alone or in the combinations according to the invention, sprayed in various dosages on to the green parts of the plants using an application rate of 600 l of water/ha (converted). For further cultivation of the plants, the pots were then again kept under optimum conditions in a greenhouse.

The visual scoring of the herbicidal effects was carried out in intervals up to 21 days after the treatment. Scoring was carried out in percent in comparison to the untreated control plants. 0%=no herbicidal activity, 100%=complete herbicidal activity=complete kill.

The percentages from the treatments with the herbicides alone (=individual application) and with the combinations according to the invention (=mixtures) were employed to calculate interactions using the method of Colby. When the observed efficacies of the mixtures exceed the formal sum of the values of the tests with individual applications, they also exceed the expected value according to Colby, which is calculated using the formula below (cf. S. R. Colby; in Weeds 15 (1967) pp. 20 to 22):

$$E = A + B - (A \times B/100)$$

Here:

A, B=activity of components A and B in percent at a dosage of a and b g of ai/ha (=gramm of active substance per hectare), respectively.

E=expected value in % at a dosage of a+b g of ai/ha.

Results

The combinations according to the invention of herbicides from group (A) with herbicides from group (B) were tested on a broad spectrum of important harmful plants (weed grasses, broad-leaved weeds/Cyperaceae) and useful plants: *Triticum aestivum* (TRZAS), *Stellaria media* (STEME), *Lolium multiflorum* (LOLMU), *Veronica persica* (VERPE), *Alopecurus myosuroides* (ALOMY), *Matricaria inodora* (MATIN), *Brassica napus* (BRSNW), *Viola tricolor* (VIOTR), *Avena fatua* (AVEFA), *Amaranthus retroflexus* (AMARE), *Zea mays* (ZEAMX), *Pharbitis purpurea* (PHBPU), *Setaria viridis* (SETVI), *Fallopia* (ex *Polygonum*) *convolvulus* (POLCO), *Echinochloa crus-galli* (ECHCG), *Abuthilon theophrasti* (ABUTH), *Cyperus esculentus* (CYPES), *Oryza sativa* (ORYSA).

Of particular interest are the results shown in the tables (Tab.) below, where the following key is used:

(1) EPPO code (former Bayer code) for the treated plant (see above)

(2) Time of scoring: DAT (days after treatment)

(3) Component A tested (identifying number)

(4) Component B tested (identifying number)

(5) Dosage component A [g of ai/ha]

(6) Dosage component B [g of ai/ha]

(7) % activity found (8) E value (calculated according to Colby; see above)

(9) Comments: "SYNERGY"=synergistic interaction (E value<% activity found); "SAFENING"=safener action on useful plant (E value>% activity found)

TABLE 1

(1) LOLMU - (2) 10 DAT - (3) A-1 - (4) B2-1

| | (5) | (6) | (7) | (8) |
|---|---|---|---|---|
| (3) | 12 | — | 10 | — |
| | 4 | — | 0 | — |
| (4) | — | 12 | 40 | — |
| (3) + (4) | 12 | 12 | 70 | 46 |
| | 4 | 12 | 70 | 40 |

(9) SYNERGY

TABLE 2

(1) ZEAMX - (2) 10 DAT - (3) A-1 - (4) B2-1

| | (5) | (6) | (7) | (8) |
|---|---|---|---|---|
| (3) | 12 | — | 0 | — |
| | 4 | — | 0 | — |
| (4) | — | 36 | 40 | — |
| | — | 12 | 40 | — |
| (3) + (4) | 12 | 36 | 70 | 40 |
| | 12 | 12 | 60 | 40 |
| | 4 | 36 | 50 | 40 |
| | 4 | 12 | 50 | 40 |

(9) SYNERGY

TABLE 3

(1) LOLMU - (2) 21 DAT - (3) A-1 - (4) B2-1

| | (5) | (6) | (7) | (8) |
|---|---|---|---|---|
| (3) | 4 | — | 0 | — |
| (4) | — | 36 | 70 | — |
| | — | 12 | 20 | — |
| (3) + (4) | 4 | 36 | 80 | 70 |
| | 4 | 12 | 60 | 20 |

(9) SYNERGY

TABLE 4

(1) LOLMU - (2) 21 DAT - (3) A-1 - (4) B2-1

| | (5) | (6) | (7) | (8) |
|---|---|---|---|---|
| (3) | 12 | — | 10 | — |
| (4) | — | 12 | 20 | — |
| (3) + (4) | 12 | 12 | 70 | 28 |

(9) SYNERGY

TABLE 5

(1) ZEAMX - (2) 21 DAT - (3) A-1 - (4) B2-1

| | (5) | (6) | (7) | (8) |
|---|---|---|---|---|
| (3) | 12 | — | 0 | — |
| | 4 | — | 0 | — |
| (4) | — | 36 | 0 | — |
| | — | 12 | 0 | — |
| (3) + (4) | 12 | 36 | 50 | 0 |
| | 12 | 12 | 40 | 0 |
| | 4 | 36 | 20 | 0 |
| | 4 | 12 | 10 | 0 |

(9) SYNERGY

TABLE 6

(1) ORYSA - (2) 21 DAT - (3) A-1 - (4) B2-1

| | (5) | (6) | (7) | (8) |
|---|---|---|---|---|
| (3) | 12 | — | 10 | — |
| | 4 | — | 0 | — |
| (4) | — | 36 | 70 | — |
| (3) + (4) | 12 | 36 | 60 | 73 |
| | 4 | 36 | 50 | 70 |

(9) SAFENING

TABLE 7

(1) TRZAS - (2) 10 DAT - (3) A-1 - (4) B4-6

| | (5) | (6) | (7) | (8) |
|---|---|---|---|---|
| (3) | 12 | — | 0 | — |
| | 4 | — | 0 | — |
| (4) | — | 9 | 50 | — |
| (3) + (4) | 12 | 9 | 60 | 50 |
| | 4 | 9 | 60 | 50 |

(9) SYNERGY

TABLE 8

(1) VIOTR - (2) 10 DAT - (3) A-1 - (4) B4-6

|  | (5) | (6) | (7) | (8) |
|---|---|---|---|---|
| (3) | 4 | — | 20 | — |
| (4) | — | 9 | 85 | — |
|  | — | 3 | 10 | — |
| (3) + (4) | 4 | 9 | 100 | 88 |
|  | 4 | 3 | 95 | 28 |

(9) SYNERGY

TABLE 9

(1) VIOTR - (2) 10 DAT - (3) A-1 - (4) B4-6

|  | (5) | (6) | (7) | (8) |
|---|---|---|---|---|
| (3) | 12 | — | 20 | — |
| (4) | — | 3 | 10 | — |
| (3) + (4) | 12 | 3 | 90 | 28 |

(9) SYNERGY

TABLE 10

(1) ZEAMX - (2) 10 DAT - (3) A-1 - (4) B4-6

|  | (5) | (6) | (7) | (8) |
|---|---|---|---|---|
| (3) | 12 | — | 0 | — |
| (4) | — | 3 | 40 | — |
| (3) + (4) | 12 | 3 | 60 | 40 |

(9) SYNERGY

TABLE 11

(1) ORYSA - (2) 10 DAT - (3) A-1 - (4) B4-6

|  | (5) | (6) | (7) | (8) |
|---|---|---|---|---|
| (3) | 12 | — | 10 | — |
|  | 4 | — | 10 | — |
| (4) | — | 9 | 40 | — |
|  | — | 3 | 40 | — |
| (3) + (4) | 12 | 9 | 30 | 46 |
|  | 12 | 3 | 30 | 46 |
|  | 4 | 9 | 20 | 46 |
|  | 4 | 3 | 20 | 46 |

(9) SAFENING

TABLE 12

(1) TRZAS - (2) 21 DAT - (3) A-1 - (4) B4-6

|  | (5) | (6) | (7) | (8) |
|---|---|---|---|---|
| (3) | 12 | — | 0 | — |
| (4) | — | 3 | 30 | — |
| (3) + (4) | 12 | 3 | 40 | 30 |

(9) SYNERGY

TABLE 13

(1) MATIN - (2) 21 DAT - (3) A-1 - (4) B4-6

|  | (5) | (6) | (7) | (8) |
|---|---|---|---|---|
| (3) | 4 | — | 50 | — |
| (4) | — | 9 | 80 | — |
| (3) + (4) | 4 | 9 | 100 | 90 |

(9) SYNERGY

TABLE 14

(1) AVEFA - (2) 21 DAT - (3) A-1 - (4) B4-6

|  | (5) | (6) | (7) | (8) |
|---|---|---|---|---|
| (3) | 12 | — | 30 | — |
|  | 4 | — | 10 | — |
| (4) | — | 3 | 0 | — |
| (3) + (4) | 12 | 3 | 40 | 30 |
|  | 4 | 3 | 40 | 10 |

(9) SYNERGY

TABLE 15

(1) ZEAMX - (2) 21 DAT - (3) A-1 - (4) B4-6

|  | (5) | (6) | (7) | (8) |
|---|---|---|---|---|
| (3) | 12 | — | 0 | — |
| (4) | — | 3 | 30 | — |
| (3) + (4) | 12 | 3 | 40 | 30 |

(9) SYNERGY

TABLE 16

(1) CYPES - (2) 21 DAT - (3) A-1 - (4) B4-6

|  | (5) | (6) | (7) | (8) |
|---|---|---|---|---|
| (3) | 4 | — | 80 | — |
| (4) | — | 9 | 20 | — |
| (3) + (4) | 4 | 9 | 98 | 84 |

(9) SYNERGY

The invention claimed is:

1. A herbicide combination comprising
(A) a compound of formula (A1) or salt thereof

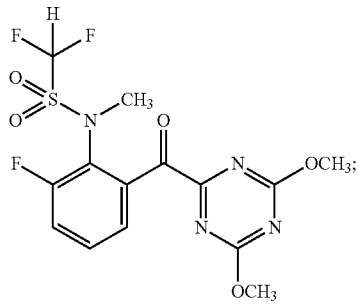

(A1)

and
(B) saflufenacil.

2. The herbicide combination as claimed in claim 1, wherein the weight ratio (A):

(B) of the components (A) and (B) is in the range of from 1:5000 to 500:1.

3. The herbicide combination as claimed in claim 1, comprising one or more further components selected from the group of agrochemically active compounds formulation auxiliaries and additives customary in crop protection.

4. The herbicide combination as claimed in claim 1, wherein the weight ratio (A):(B) of the components (A) and (B) is in the range of from 1:1000 to 250:1.

5. The herbicide combination as claimed in claim 1, wherein the weight ratio (A):(B) of the components (A) and (B) is in the range of from 1:160 to 100:1.

6. The herbicide combination as claimed in claim 1, further comprising a herbicide that is herbicidally active based on inhibition of acetolactate synthase, acetyl coenzyme A carboxylase, cellulose synthase, enolpyruvylshikimate 3-phosphate synthase, glutamine synthetase, p-hydroxyphenylpyruvate dioxygenase, phytoene desaturase, or protoporphyrinogen oxidase.

7. The herbicide combination as claimed in claim 1, further comprising a safener, wherein the weight ratio of the components (A) and (B): safener is in the range of from 3000:1 to 1:500.

8. A method for controlling a weed, the method comprising separately or jointly applying to one or more of a plant, a seed, or an area under cultivation (A) a compound of formula (A1) or salt thereof

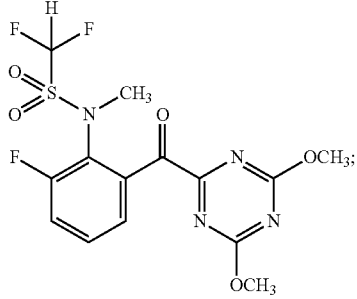

and
(B) saflufenacil.

9. The method as claimed in claim 8 wherein said weed is controlled in a crop plant selected from wheat, durum wheat, common wheat, corn, soybeans, sugar beet, sugar cane, cotton, rice, beans, flax, barley, oats, rye, triticale, oilseed rape, potatoes, millet, sorghum, pasture grass, greens/lawns; in a fruit plantation crop; or on a non-crop area.

10. The method as claimed in claim 8 wherein the components (A) and (B) are applied jointly.

11. The method as claimed in claim 8 wherein the components (A) and (B) are applied separately.

12. The method as claimed in claim 8 wherein said weed is controlled in rice.

13. The method as claimed in claim 8 wherein said weed comprises a plant selected from one or more of the group consisting of broad-leaved weeds, weed grasses, and Cyperaceae that are resistant to herbicidally active compounds selected from the group consisting of glyphosate, glufosinate, atrazine, imidazolinone herbicides, sulfonylureas, (hetero) aryloxyaryloxyalkylcarboxylic acids, -phenoxyalkylcarboxylic acids, cyclohexanedione oximes, and auxin inhibitors.

14. The method as claimed in claim 8, wherein the weight ratio (A) : (B) of the components (A) and (B) is in the range of from 1:1000 to 250:1.

15. The method as claimed in claim 8, wherein the weight ratio (A) : (B) of the components (A) and (B) is in the range of from 1:160 to 100:1.

16. The method as claimed in claim 8, wherein component (A) is applied at an application rate 0.1-1000 g of active substance per hectare.

17. The method as claimed in claim 8, wherein component (A) is applied at an application rate 0.1-500 g of active substance per hectare.

18. The method as claimed in claim 8, wherein component (B) is applied at an application rate 1-1000 g of active substance per hectare.

19. The method as claimed in claim 8, wherein component (B) is applied at an application rate 2-800 g of active substance per hectare.

* * * * *